United States Patent
Lietzau et al.

(10) Patent No.: US 7,182,885 B2
(45) Date of Patent: Feb. 27, 2007

(54) FLUORINATED INDENES AND 1,7-DIHYDROINDACENES OF NEGATIVE DIELECTRIC ANISOTROPY

(75) Inventors: Lars Lietzau, Darmstadt (DE); Melanie Klasen-Memmer, Heuchelheim (DE); Matthias Bremer, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/406,569

(22) Filed: Apr. 4, 2003

(65) Prior Publication Data
US 2003/0222243 A1 Dec. 4, 2003

(30) Foreign Application Priority Data
Apr. 4, 2002 (DE) ............... 102 14 938

(51) Int. Cl.
*C09K 19/32* (2006.01)
*C07C 43/21* (2006.01)
*C07C 25/22* (2006.01)

(52) U.S. Cl. .................. 252/299.62; 252/299.63; 252/299.66; 568/634; 570/126; 570/127; 570/128; 570/129; 570/131; 349/184

(58) Field of Classification Search ........... 570/126, 570/129, 131, 127, 128; 568/634; 252/299.01, 252/299.62, 299.63, 299.66; 349/184
See application file for complete search history.

(56) References Cited

U.S. PATENT DOCUMENTS

| 3,828,795 | A | * | 8/1974 | Schumacher et al. | ....... | 131/277 |
| 5,204,017 | A | * | 4/1993 | Reiffenrath et al. | .... | 252/299.61 |
| 5,789,634 | A | * | 8/1998 | Sullivan et al. | ............ | 570/183 |
| 2004/0171866 | A1 | * | 9/2004 | Reiffenrath et al. | ........... | 560/86 |

FOREIGN PATENT DOCUMENTS

JP 06-234973 * 8/1994

OTHER PUBLICATIONS

Barnette, W. E., N-Fluoro-N-alkylsulfonamides: useful reagents for the fluorination of carbanions, Jan. 1984, Journal of the American Chemical Society, vol.106, No. 2, pp. 452-454.*

McClinton, Martin A., First trapping of 5,5-difluorocyclopentadiene, Sep. 1992, Journal of the Chemical Society, Perkins Transactions 1: Organic and Bio-organic Chemistry, Issue 17, pp. 249-250.*

\* cited by examiner

*Primary Examiner*—Rosalynd Keys
(74) *Attorney, Agent, or Firm*—Miller, White, Zelano, Branigan, P.C.

(57) ABSTRACT

Fluorinated indenes and 1,7-dihydroindacenes of the general formulae (I) and (II) of negative dielectric anisotropy ($\Delta\epsilon < 0$)

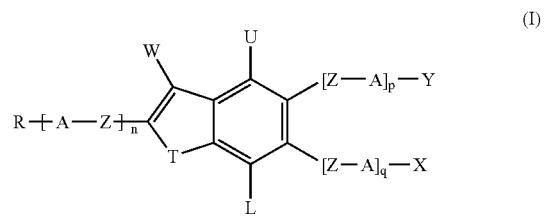

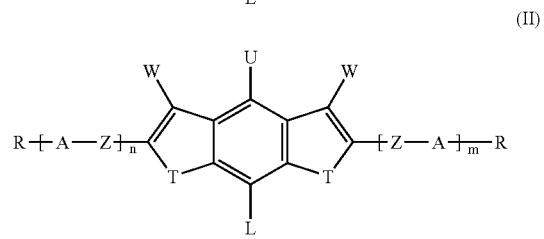

in which
T, A, R, L, X, Y, U, W, Z, n, m, p and q are as defined herein are suitable for use in liquid crystal display elements.

30 Claims, No Drawings

FLUORINATED INDENES AND 1,7-DIHYDROINDACENES OF NEGATIVE DIELECTRIC ANISOTROPY

The invention relates to fluorinated indenes and 1,7-dihydroindacenes of negative $\Delta\epsilon$ and to the use thereof in liquid-crystalline media.

Liquid crystals have found widespread use since the first commercially usable liquid-crystalline compounds were found about 30 years ago. Known areas of application are, in particular, displays for watches or pocket calculators, and large display panels as used in railway stations, airports and sports arenas. Further areas of application are displays of portable computers or navigation systems and video applications. For the last-mentioned applications in particular, high demands are made of the response times and contrast of the images.

le;2qThe spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacity; in other words, the dielectric constant $\epsilon$ of the liquid crystal has different values for the two orientations. Substances whose dielectric constant is larger when the longitudinal axes of the molecules are aligned perpendicular to the capacitor plates than when they are aligned parallel are known as being dielectrically positive. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as nitrile groups (—CN) or fluorine, into the liquid-crystal molecules enables a broad range of working voltages to be achieved.

In the liquid-crystalline molecules used in conventional liquid-crystal displays, the dipole moment oriented along the longitudinal axis of the molecules is larger than the dipole moment oriented perpendicular to the longitudinal axis of the molecules. An improvement in the viewing-angle dependence is only possible with very great effort, for example film compensation. In the most widespread TN cells ("twisted nematic"), a liquid-crystalline layer with a thickness of only from about 3 to 10 μm is arranged between two flat glass plates, onto each of which an electrically conductive, transparent layer of tin oxide or indium tin oxide has been vapour-deposited as electrode. A likewise transparent alignment layer, usually consisting of a plastic (for example polyimides), is located between these films and the liquid-crystalline layer. This alignment layer serves to bring the longitudinal axes of the adjacent crystalline molecules into a preferential direction through surface forces in such a way that, in the voltage-free case, they lie uniformly on the inside of the display surface with the same alignment in a flat manner or with the same small tilt angle. Two polarisation films which only enable linear-polarised light to enter and escape, are adhesively bonded to the outside of the display in certain arrangements.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality drops drastically under certain circumstances. Attempts have recently been made to improve the viewing-angle dependence using liquid-crystalline compounds whose dipole moment perpendicular to the longitudinal axis of the molecules is larger than that parallel to the longitudinal axis of the molecule. In the field-free state, the molecules are aligned perpendicular to the glass surface of the display. Displays of this type are known as VA-TFT displays ("vertical aligned"). In an applied field, the molecules orient themselves with their longitudinal axes perpendicular to the field lines. The so-called multidomain technique has enabled an improvement in the viewing-angle dependence to be achieved.

The development in the area of liquid-crystalline materials is far from complete. In order to improve the properties of liquid-crystalline display elements, attempts are constantly being made to develop novel compounds which enable displays of this type to be optimised.

An object of the invention is therefore to provide compounds having advantageous properties which form liquid-crystalline phases.

Upon further study of the specification and appended claims, further objects and advantages of this invention will become apparent to those skilled in the art.

These objects are achieved by indenes and 1,7-dihydroindacenes of the general formulae (I) and (II) respectively

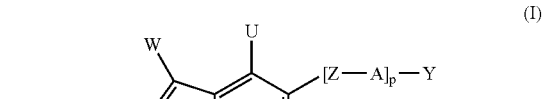

(I)

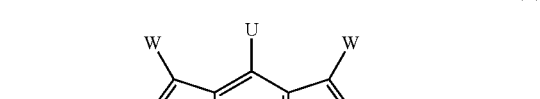

(II)

in which:
T is in each case, independently of one another,

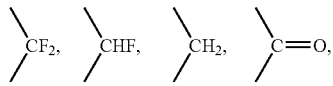

A is in each case, independently of one another, 1,4-phenylene, in which one or two =CH— groups are each, optionally, replaced by =N—, and which is unsubstituted or monosubstituted to tetrasubstituted, independently of one another, by halogen (—F, —Cl, —Br, or —I), —CN, —CH$_3$, —CH$_2$F, —CHF$_2$, —CF$_3$, —OCH$_3$, —OCH$_2$F, —OCHF$_2$ or —OCF$_3$, or is 1,4-cyclohexylene, 1,4-cyclohexenylene or 1,4-cyclohexadienylene, in which one or two —CH$_2$— groups are each, optionally, independently of one another, replaced by —O— or —S—, and which is unsubstituted or mono- or polysubstituted by halogen,
R is in each case, independently of one another, hydrogen, an alkyl radical, alkoxy radical, alkenyl radical or alkynyl radical having from 1 to 15 or 2 to 15 carbon atoms respectively which is unsubstituted, monosubstituted by —CF$_3$ or at least monosubstituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, or is halogen, —CN, —SCN, —NCS, —SF$_5$, —CF$_3$, —OCF$_3$, —OCHF$_2$ or —OCH$_2$F,
L is hydrogen or halogen,
X is hydrogen, an alkyl radical, alkoxy radical, alkenyl radical or alkynyl radical having from 1 to 15 or 2 to 15 carbon atoms respectively which is unsubstituted, monosubstituted by —CF$_3$ or at least monosubstituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent, or is halogen, —CN, —SCN or —NCS,
Y, U and W, independently of one another, are hydrogen, an alkyl radical, alkoxy radical, alkenyl radical or alkynyl radical having from 1 to 15 or 2 to 15 carbon atoms respectively which is unsubstituted, monosubstituted by —CF$_3$ or at least monosubstituted by halogen, where, in addition, one or more CH$_2$ groups in these radicals may each, independently of one another, be replaced by —O—, —S—, —CO—, —COO—, —OCO— or —OCO—O— in such a way that heteroatoms are not directly adjacent,
Z is in each case, independently of one another, a single bond, —CF$_2$O—, —OCF$_2$—, —CH$_2$CH$_2$—, —CF$_2$CF$_2$—, —C(O)O—, —OC(O)—, —CH$_2$O—, —OCH$_2$—, —CF=CH—, —CH=CF—, —CF=CF—, —CH=CH— or —C≡C—,
n and m, independently of one another, are 0, 1, 2 or 3,
p and q, independently of one another, are 0, 1, 2 or 3,
with the proviso that, in the formula (I), L=—F if

and p and q are each 0.

All the compounds have a negative Δε and are therefore suitable for use in VA-TFT displays. They exhibit very good compatibility with the conventional substances used in liquid-crystal mixtures for displays.

The fluorine substituents in the indene or 1,7-dihydroindacene structure produce a dipole moment perpendicular to the longitudinal molecular axis, which, if desired, can be increased further by means of suitable substituents in the wing units -[A–Z]$_{m,n,p,\text{ or }q}$-R. In the field-free state, the compounds of the formulae (I) and (II) align themselves with their longitudinal molecular axis perpendicular to the treated or coated glass surface of a display.

In the general formulae (I) and (II), A is preferably, independently of one another, optionally substituted 1,4-phenylene, optionally substituted 1,4-cyclohexylene, in which —CH$_2$— may be replaced once or twice by —O—, or optionally substituted 1,4-cyclohexenylene. A is particularly preferably, independently of one another,

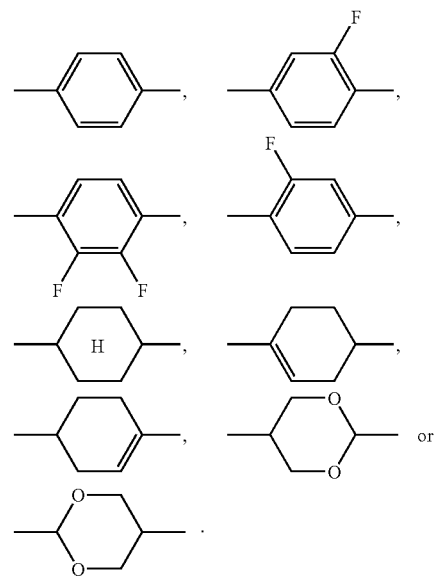

If L is halogen, it is preferably fluorine or chlorine, particularly preferably fluorine.

R, X, Y, U and W in the general formulae (I) and (II) may each, independently of one another, be an alkyl radical and/or an alkoxy radical having from 1 to 15 carbon atoms, which may be straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, methoxy, ethoxy, propoxy, butoxy, pentoxy, hexyloxy or heptyloxy.

R, X, Y, U and W may each, independently of one another, be oxaalkyl, preferably straight-chain 2-oxapropyl (=methoxymethyl), 2-(=ethoxy-methyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl.

R, X, Y, U and W may each, independently of one another, be an alkenyl radical having from 2 to 15 carbon atoms, which may be straight-chain or branched. It is preferably straight-chain and has from 2 to 7 carbon atoms.

Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or-6-enyl.

R, X, Y, U and W may each, independently of one another, be an alkyl radical having from 1 to 15 carbon atoms in which one CH$_2$ group has been replaced by —O— and one has been replaced by —CO—, where these are preferably adjacent. This thus contains an acyloxy group —CO—O— or an oxycarbonyl group —O—CO—. This is preferably straight-chain and has from 2 to 6 carbon atoms.

R, X, Y, U and W may each, independently of one another, be an alkyl radical having from 1 to 15 carbon atoms in which one CH$_2$ group has been replaced by unsubstituted or substituted —CH═CH— and an adjacent CH$_2$ group has been replaced by —CO—, —CO—O— or —O—CO—, where this may be straight-chain or branched. It is preferably straight-chain and has from 4 to 13 carbon atoms.

R, X, Y, U and W may each, independently of one another, be an alkyl radical having from 1 to 15 carbon atoms or alkenyl radical having from 2 to 15 carbon atoms, each of which is monosubstituted by —CN or —CF$_3$ and is preferably straight-chain. The substitution by —CN or —CF$_3$ is in any desired position.

R, X, Y, U and W may each, independently of one another, be an alkyl radical having from 1 to 15 carbon atoms or an alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —CF$_3$. In the case of monosubstitution, the fluorine or chlorine substituent can be in any desired position, but is preferably in the ω-position.

R, X, Y, U and W may each, independently of one another, be an alkyl radical in which two or more CH$_2$ groups are each replaced by —O— or —CO—O—, where this may be straight-chain or branched. It is preferably branched and has from 3 to 12 carbon atoms.

R in the general formulae (I) and (II) is preferably in each case, independently of one another, an alkyl radical, alkoxy radical or alkenyl radical having from 1 to 7 or 2 to 7 carbon atoms respectively.

Preferred bridging groups Z in the compounds of the general formulae (I) and (II) are each, independently of one another, a single bond, —CF$_2$O—, —OCF$_2$—, —CF$_2$CF$_2$—, —CH═CH—, —CF═CH—, —CH═CF— or —CF═CF—.

U and W in the formula (I) or formula (II) are preferably hydrogen.

Preferred substituents X and Y in the general formula (I) are hydrogen, an alkyl radical, alkoxy radical or alkenyl radical having from 1 to 7 or 2 to 7 carbon atoms respectively, such as the above-mentioned straight-chain alkyl, alkoxy and alkenyl radicals.

X may additionally be halogen, —CN, —SCN or —NCS. It is preferably halogen, in particular fluorine.

The compounds of the general formulae (I) and (II) preferably have at least one lateral fluorine substituent on the indene or 1,7-dihydroindacene structure, i.e. T, L and/or X in the formula (I) and T and/or L in the formula (II) contain at least one fluorine. If

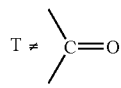

in the formula (I) or formula (II), T, L and X in the formula (I) preferably contain from 2 to 4 fluorine atoms and T and L in the formula (11) preferably contain from 3 to 5 fluorine atoms.

Preferred indenes of the general formula (I) have one or two rings A, i.e. n+p+q=1 or 2.

Preferred 1,7-dihydroindacenes of the general formula (II) preferably have one or two rings A, i.e. n+m=1 or 2.

Examples of indenes and 1,7-dihydroindacenes according to the invention are the following compounds:

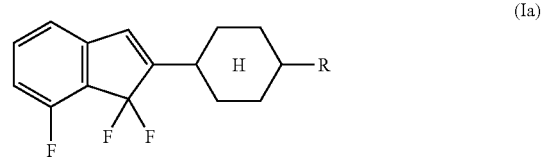

(Ia)

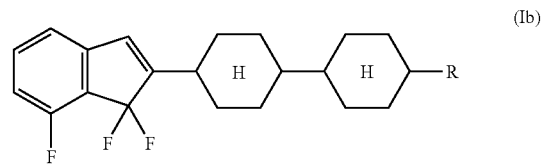

(Ib)

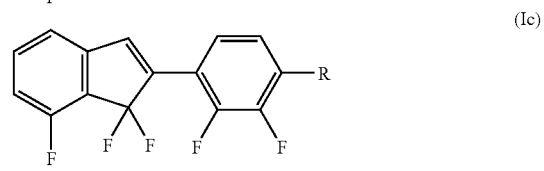

(Ic)

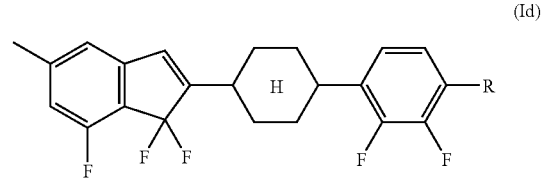

(Id)

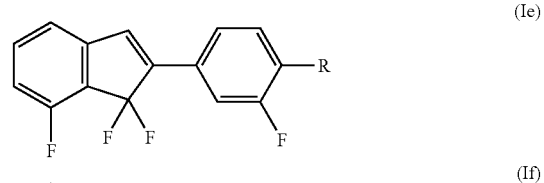

(Ie)

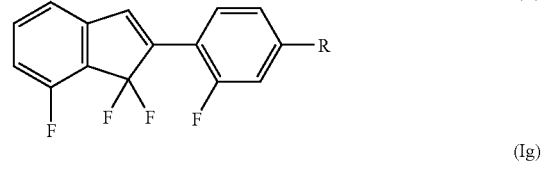

(If)

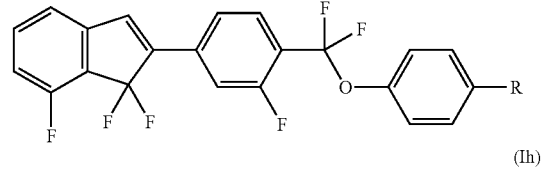

(Ig)

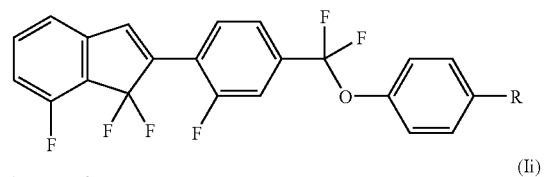

(Ih)

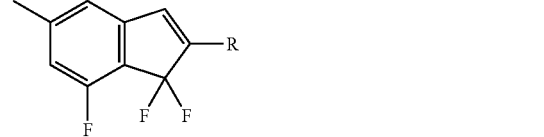

(Ii)

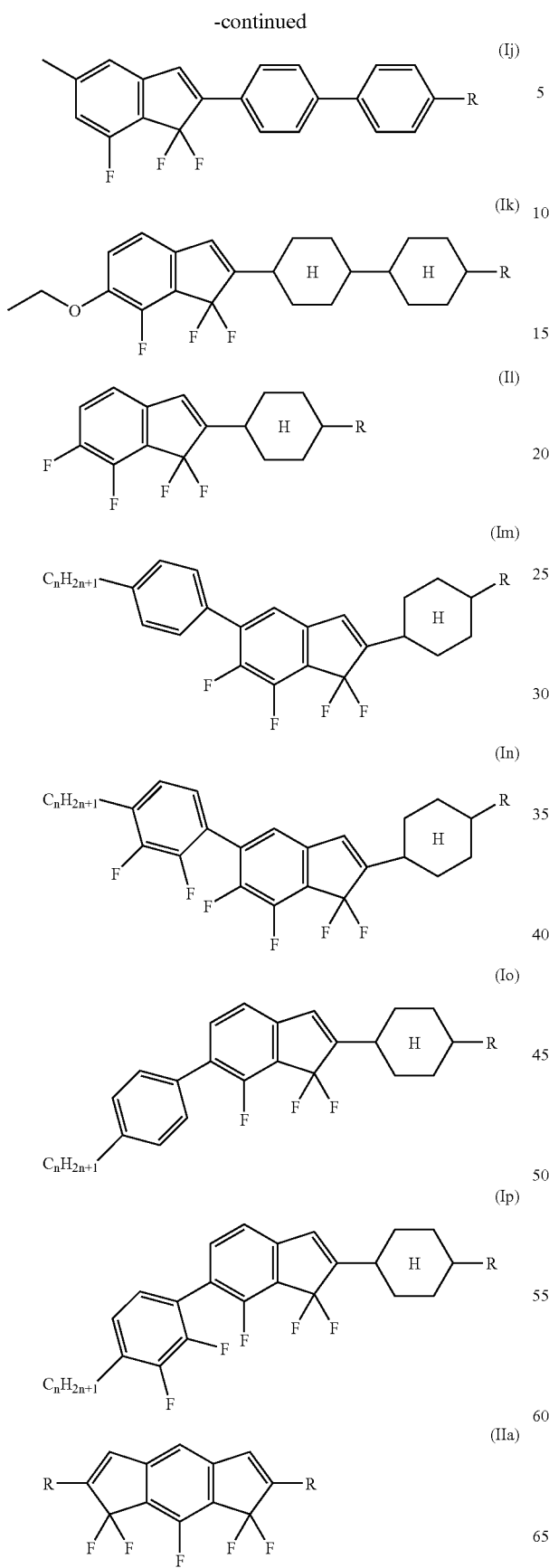
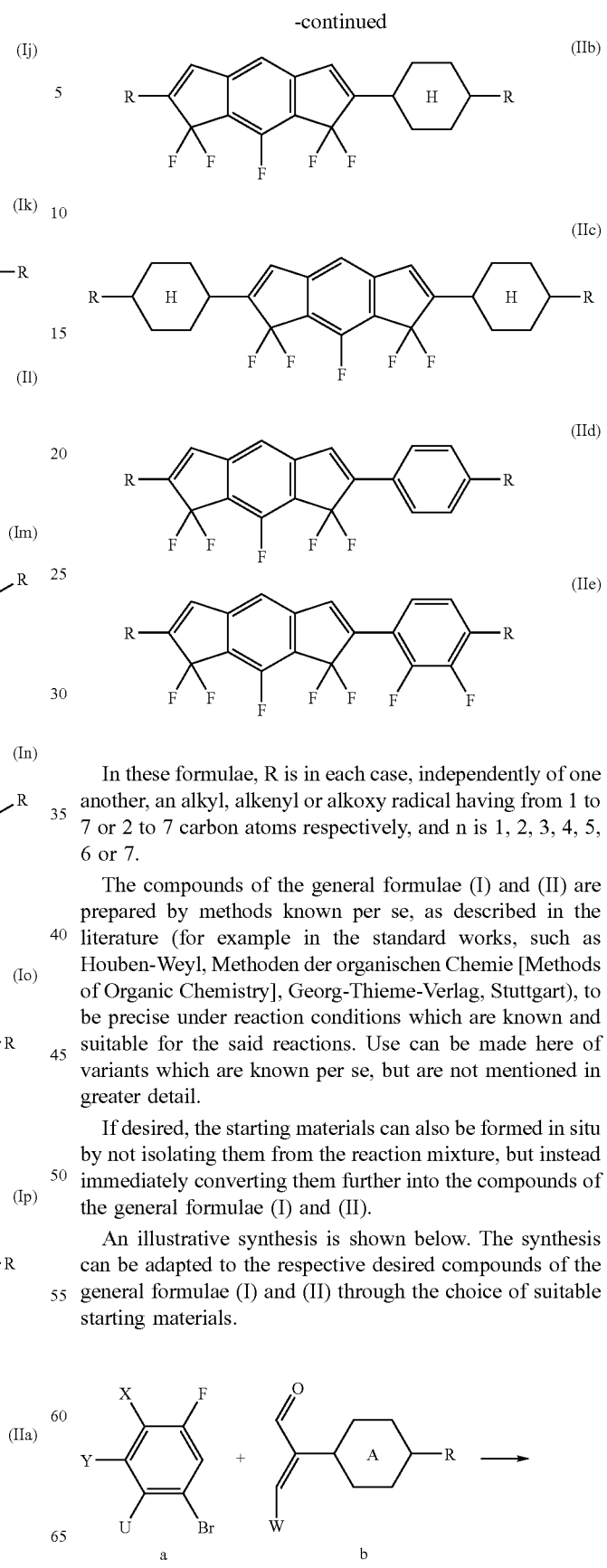

In these formulae, R is in each case, independently of one another, an alkyl, alkenyl or alkoxy radical having from 1 to 7 or 2 to 7 carbon atoms respectively, and n is 1, 2, 3, 4, 5, 6 or 7.

The compounds of the general formulae (I) and (II) are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants which are known per se, but are not mentioned in greater detail.

If desired, the starting materials can also be formed in situ by not isolating them from the reaction mixture, but instead immediately converting them further into the compounds of the general formulae (I) and (II).

An illustrative synthesis is shown below. The synthesis can be adapted to the respective desired compounds of the general formulae (I) and (II) through the choice of suitable starting materials.

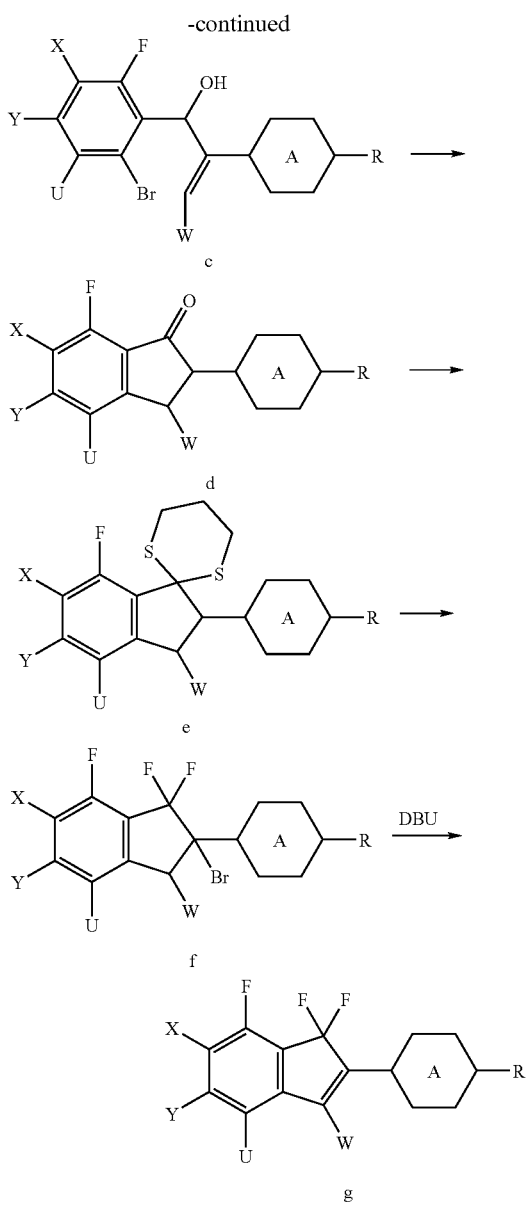

Starting from 3-bromofluorobenzene a, reaction with the α,β-unsaturated aldehyde b in the presence of lithium diisopropylamide (LDA) gives compound c. This reacts with palladium catalysis in the presence of triethylamine with ring closure to give the indanone d. From the indanone d and 1,3-propanedithiol in the presence of $BF_3$ diethyl ether, the corresponding dithiane e is obtained. This is reacted with 1,3-dibromo-5,5-dimethylhydantoin (DBH) and HF in pyridine to give the trifluorobromo-indane f. Elimination of HBr in the presence of diazabicycloundecene (DBU) gives the trifluoroindene g.

The 1,7-dihydroindacene (II) is obtained analogously by starting from 3,5-dibromofluorobenzene instead of the (substituted) 3-bromofluorobenzene.

The reactions depicted should only be regarded as illustrative. The person skilled in the art can carry out corresponding variations of the syntheses shown and also follow other suitable synthetic routes to give compounds of the formulae (I) and (II).

As already mentioned, the compounds of the general formulae (I) and (II) can be used for the preparation of liquid-crystalline mixtures. The invention therefore also relates to a liquid-crystalline medium comprising at least two liquid-crystalline compounds, including at least one compound of the general formulae (I) and/or (II).

The present invention also relates to liquid-crystalline media comprising from 2 to 40, preferably from 4 to 30, components as further constituents besides one or more compounds of the formulae (I) and/or (II) according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, ter-phenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenyl-cyclohexanes, cyclohexylbiphenyls, phenylcyclohexylcyclohexanes, cyclo-hexylcyclohexanes, cyclohexylcyclohexylcyclohexenes, 1,4-biscyclohexyl-benzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae (III), (IV), (V), (VI) and (VII):

R'-L-E-R" (III)

R'-L-COO-E-R" (IV)

R'-L-OOC-E-R" (V)

R'-L-$CH_2CH_2$-E-R" (VI)

R'-L-$CF_2$O-E-R" (VII)

In the formulae (III), (IV), (V), (VI) and (VII), L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)ethyl.

One of the radicals L and E is preferably Cyc or Phe. E is preferably Cyc, Phe or Phe-Cyc. The media according to the invention preferably comprise one or more components selected from the compounds of the formulae (III), (IV), (V), (VI) and (VII) in which L and E are selected from the group consisting of Cyc or Phe and simultaneously one or more components selected from the compounds of the formulae (III), (IV), (V), (VI) and (VII) in which one of the radicals L and E is selected from the group consisting of Cyc or Phe and the other radical is selected from the group consisting of -Phe-Phe-, -Phe-Cyc-, -Cyc-Cyc-, -G-Phe- and -G-Cyc-, and optionally one or more components selected from the compounds of the formulae (III), (IV), (V), (VI) and (VI) in which the radicals L and E are selected from the group consisting of -Phe-Cyc-, -Cyc-Cyc-, -G-Phe- and -G-Cyc-.

In a smaller sub-group of the compounds of the formulae (III), (IV), (V), (VI) and (VII), R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae (IIIa), (IVa), (Va), (VIa) and (VIIa). In most of these compounds, R' and R" are different from one another, one of these radicals usually being alkyl, alkenyl, alkoxy or alkoxyalkyl.

In another smaller sub-group of the compounds of the formulae (III), (IV), (V), (VI) and (VII), which is known as group B, E is

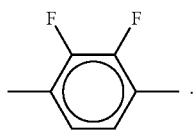

In the compounds of group B, which are referred to by the sub-formulae (IIIb), (IVb), (Vb), (VIb) and (VIIb), R' and R" are as defined for the compounds of the sub-formulae (IIIa) to (VIIa) and are preferably alkyl, alkenyl, alkoxy or alkoxyalkyl.

In a further smaller sub-group of the compounds of the formulae (III), (IV), (V), (VI) and (VII), R" is —CN. This sub-group is referred to below as group C, and the compounds of this sub-group are correspondingly described by sub-formulae (IIIc), (IVc), (Vc), (VIc) and (VIIc). In the compounds of the sub-formulae (IIIc), (IVc), (Vc), (VIc) and (VIIc), R' is as defined for the compounds of the sub-formulae (IIIa) to (VIIa) and is preferably alkyl, alkoxy or alkenyl.

Besides the preferred compounds of groups A, B and C, other compounds of the formulae (III), (IV), (V), (VI) and (VII) having other variants of the proposed substituents are also customary. All these substances are obtainable by methods which are known from the literature or analogously thereto.

Besides the compounds of the general formulae (I) and/or (II) according to the invention, the media according to the invention preferably comprise one or more compounds selected from group A and/or group B and/or group C. The proportions by weight of the compounds from these groups in the media according to the invention are preferably:

group A: from 0 to 90%, preferably from 20 to 90%, in particular from 30 to 90%
group B: from 0 to 80%, preferably from 10 to 80%, in particular from 10 to 70%
group C: from 0 to 80%, preferably from 5 to 80%, in particular from 5 to 50%,
the sum of the proportions by weight of the group A and/or B and/or C compounds present in the respective media according to the invention preferably being from 5 to 90% and in particular from 10 to 90%.

The media according to the invention preferably comprise from 1 to 40%, in particular from 5 to 30%, of compounds of the formulae (i) and/or (II) according to the invention. Preference is furthermore given to media comprising more than 40%, in particular from 45 to 90%, of compounds of the formulae (I) and/or (II) according to the invention. The media preferably comprise three, four or five compounds of the formulae (I) and/or (II) according to the invention.

Examples of the compounds of the formulae (III), (IV), (V), (VI) and (VII) are the compounds listed below:

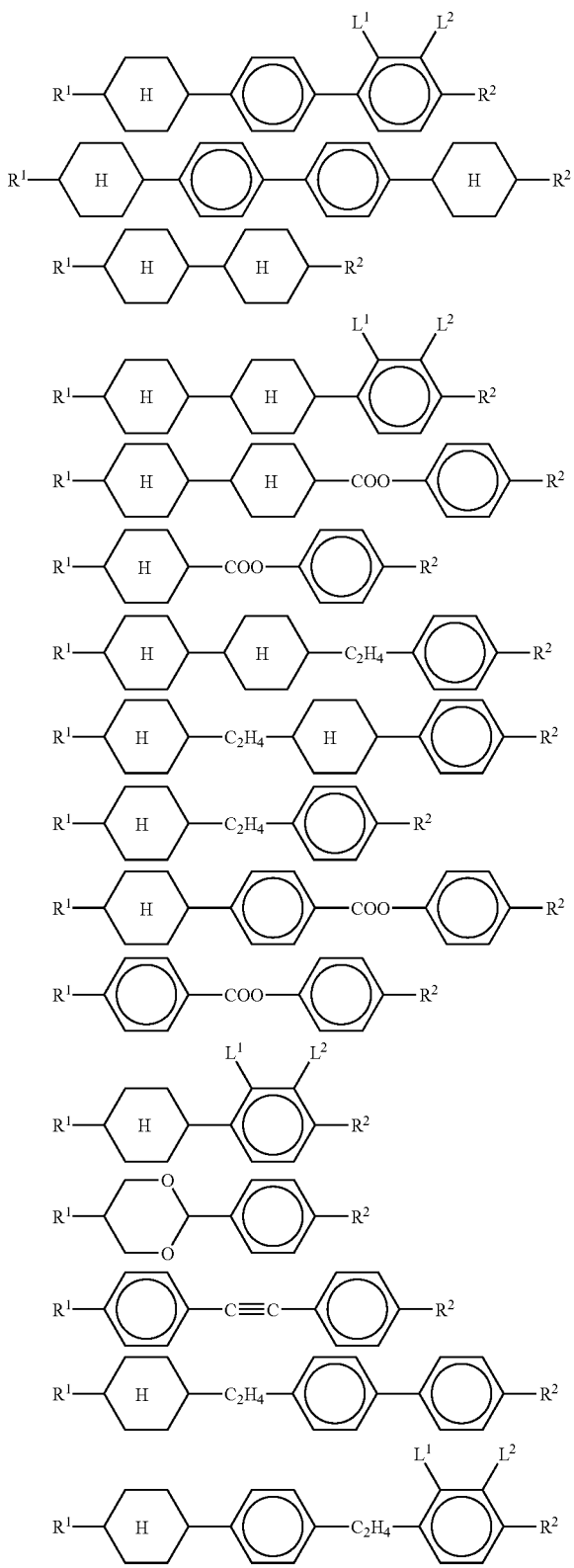

-continued

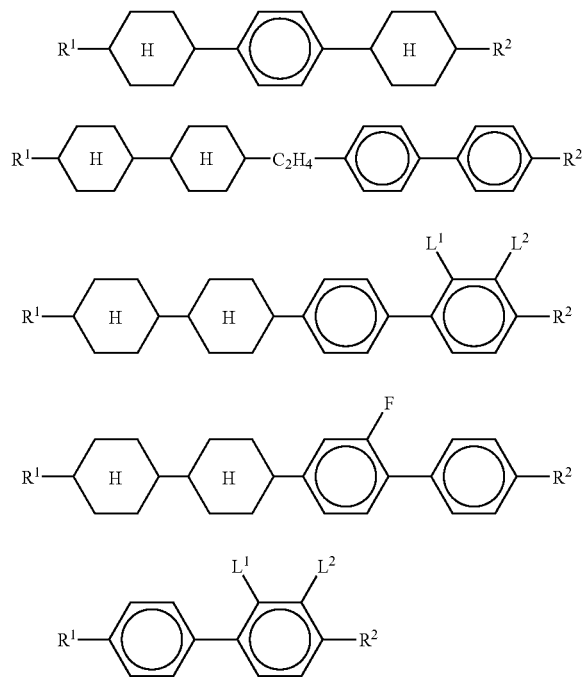

where $R^1$ and $R^2$=—$C_nH_{2n+1}$, —$C_nH_{2n-1}$ or —$OC_nH_{2n+1}$, n=1 to 8, and $L^1$ and $L^2$=—H or —F, where m and n=1 to 8.

The media according to the invention are prepared in a manner conventional per se. In general, the components are dissolved in one another, advantageously at elevated temperature. By means of suitable additives, the liquid-crystalline phases in accordance with the invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the preparation of coloured guest-host systems or substances can be added in order to modify the dielectric anisotropy, the viscosity and/or the alignment of the nematic phases.

Owing to their negative $\Delta\epsilon$, the compounds of the formulae (I) and (II) are suitable for use in VA-TFT displays. The invention therefore also relates to an electro-optical liquid-crystal display containing a liquid-crystalline medium according to the invention.

The invention is explained in greater detail by the following examples.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 10214938.0, filed Apr. 4, 2002, is hereby incorporated by reference.

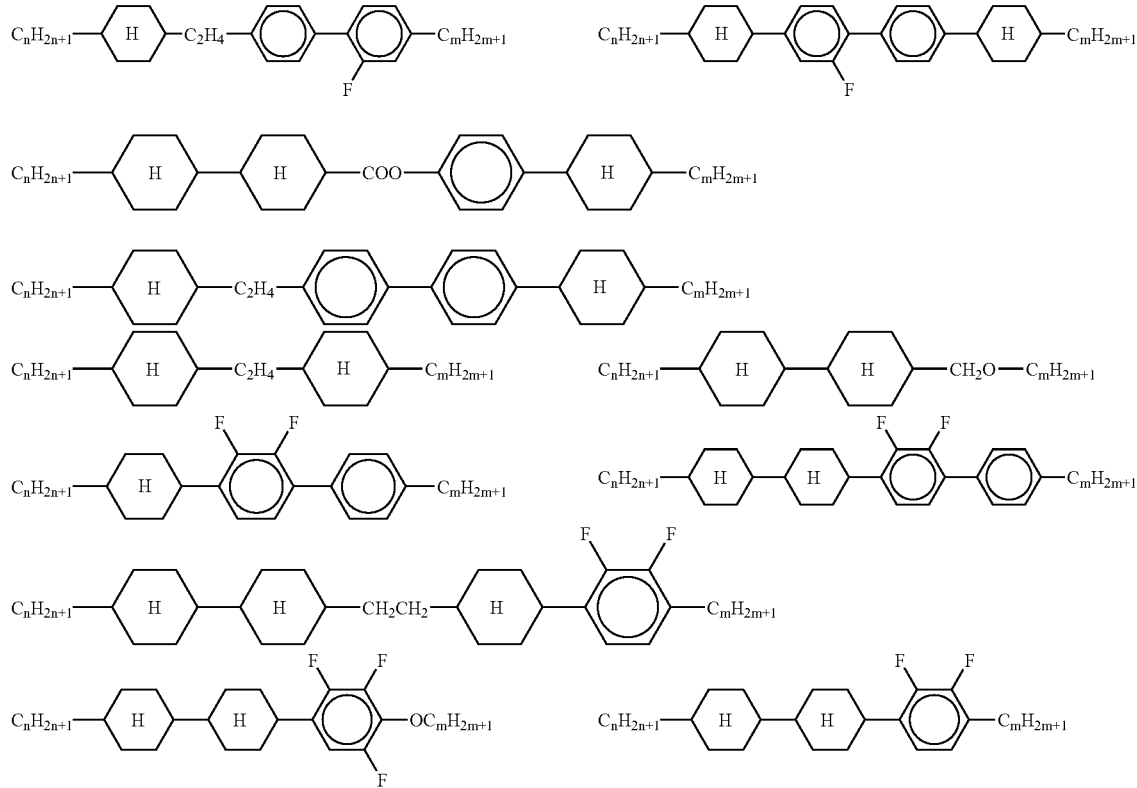

EXAMPLES

The starting substances can be obtained in accordance with generally available literature procedures or commercially. The reactions described are known from the literature.

Example 1

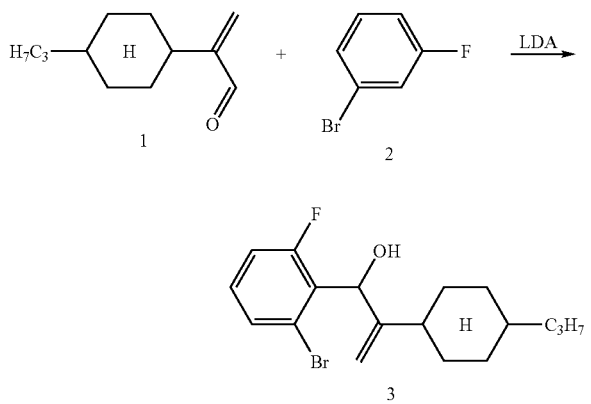

At −75° C., a solution of 7.0 ml (62.0 mmol) of bromofluorobenzene 2 in 10 ml of THF is added to 27.0 ml of a solution of 2N LDA in cyclohexane/ethylbenzene/THF (52.4 mmol) which has been diluted with 100 ml of THF. After 2 hours at the low temperature, 8.2 g (45.6 mmol) of the aldehyde 1 in 10 ml of THF are added. After 30 minutes, the cooling is removed, and 100 ml of 1N HCl are added to the batch at 20° C. Extraction of the aqueous phase, drying of the organic phase, evaporation and chromatography gives 13.5 g (83% of theory) of the allyl alcohol 3.

Example 2

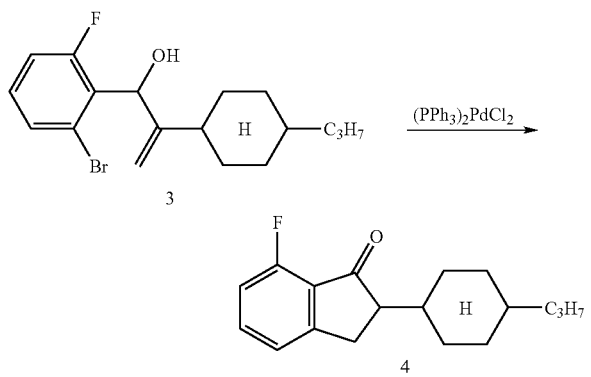

39.5 g (11.2 mmol) of the allyl alcohol 3, 5.5 g of bis(tri-o-tolylphosphine)-palladium dichloride and 50 ml of triethylamine are dissolved in 390 ml of acetonitrile and warmed to 90° C. until all the allyl alcohol has reacted. The cooled batch is introduced into water. Extraction, drying, evaporation and chromatography gives 23.2 g (76% of theory) of the indanone 4.

Example 3

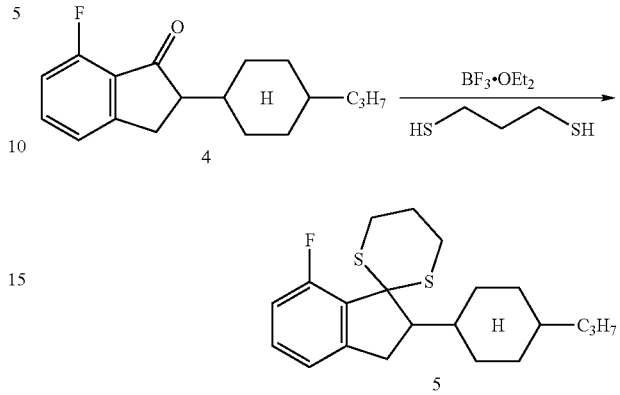

4.8 g (17.5 mmol) of the indanone 4 and 1.8 ml (17.6 mmol) of propanedithiol are dissolved in 30 ml of dichloromethane, 4.0 ml of boron trifluoride/diethyl ether complex are added at from 6 to 7° C., and the mixture is subsequently stirred overnight at room temperature. The batch is introduced into 10 ml of saturated sodium hydrogencarbonate solution and stirred until the evolution of gas is complete. After extraction of the aqueous phase, drying of the organic phase, evaporation and filtration through silica gel, the resultant residue is employed in the next step without further purification.

Example 4

5.0 g of the crude thioketal 5 in 25 ml of dichloromethane are added slowly at −75° C. to a mixture of 17.0 g (59.5 mmol) of DBH, 60 ml of a 65% by weight solution of HF in pyridine and 35 ml of dichloromethane. The batch is subsequently stirred overnight at room temperature. The reaction mixture is introduced into ice-cold hydrogen sulfite solution and deacidified using saturated sodium hydrogencarbonate solution and sodium hydroxide solution. Extraction, drying, evaporation, re-washing with water, chromatography and crystallisation from hexane gives 2.3 g of the trifluorobromo-indane 6.

Example 5

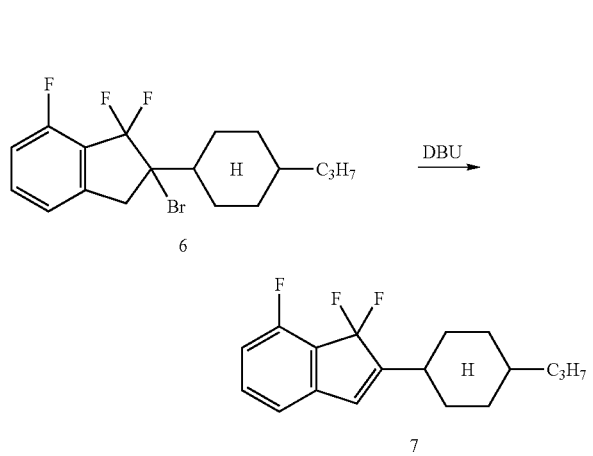

2.8 g (7.5 mmol) of the bromoindane 6 are dissolved in 25 ml of dichloromethane, 1.2 ml (8.0 mmol) of DBU are added, and the mixture is stirred at room temperature until all the starting material has reacted. The batch is washed with water and saturated sodium chloride solution, evaporated and chromatographed, giving 1.8 g (84% of theory) of the indene 7.

Spectroscopic data: ME (EI): M=294 1H-NMR: 7.20–7.32 ppm, m (1H, Ar—H), 6.75–7.90 ppm; (2H, Ar—H); 6.32 ppm, s, (1H, 3-H).

Δε=−6.1

Δn=0.107

Example 6

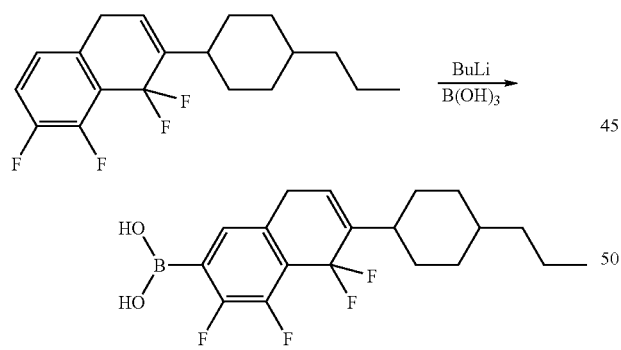

Under a nitrogen atmosphere, 2.0 g (7.2 mmol) of indene are dissolved in 50 ml of THF, and the mixture is cooled to −70° C. At this temperature, 4.5 ml (7.2 mmol) of a 15% butyllithium solution in n-hexane are added to the batch. After 1 hour, 0.9 ml (8.0 mmol) of trimethyl borate dissolved in 10 ml of THF is carefully added to the solution. The batch is warmed to 10° C. and hydrolysed. The reaction mixture is acidified using 2N HCl solution. The aqueous phase is extracted with methyl tert-butyl ether, and the organic phase is dried and evaporated. The resultant residue is processed further without further purification.

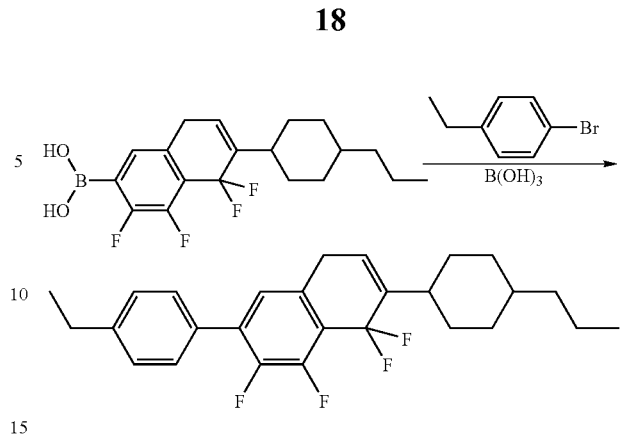

Under a nitrogen atmosphere, 1.3 g (5.0 mmol) of sodium metaborate octahydrate are dissolved in 2.0 ml of water, and 83 mg of bis(triphenyl-phosphine)palladium(II) chloride, 50 μl of hydrazinium hydroxide and 1.11 g (6.0 mmol) of p-bromoethylbenzene are added successively. After 5 minutes at room temperature, 2.2 g (6.0 mmol) of the boronic acid dissolved in 3.75 ml of THF are added to the batch, and the mixture is heated at the boil overnight. The aqueous phase is extracted with methyl tert-butyl ether, and the organic phase is washed with water, dried and evaporated. Purification is carried out by means of multiple chromatography on silica gel (heptane).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An indene compound of formula (I) having a negative dielectric anisotropy:

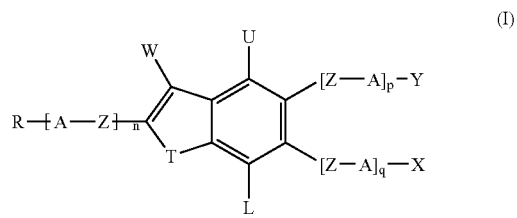

wherein:

T is in each case, independently of one another,

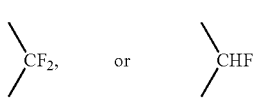

A is in each case, independently of one another, 1,4-phenylene, in which one or two =CH— groups are each, optionally, replaced by =N—, and which is unsubstituted or monosubstituted to tetrasubstituted, independently of one another, by halogen, —CN, —CH$_3$, —CH$_2$F, —CHF$_2$, —CF$_3$, —OCH$_3$, —OCH$_2$F, —OCHF$_2$ or —OCF$_3$, or is 1,4-cyclohexylene, 1,4- cyclohexenylene or 1,4-cyclohexadienylene, in which one or two —CH$_2$— groups are each, optionally, independently of one another, replaced by —O— or —S—, and which is unsubstituted or mono- or polysubstituted by halogen;

R is in each case, independently of one another, hydrogen, or is alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$ or at least monosubstituted by halogen, an wherein one or more CH$_2$ groups are, optionally, each, independently of one another, replaced by —O—, —S—, —CO—, —COO—, —OCO— or —OCO—O— in such a way that heteroatoms are not directly adjacent, or is halogen, —CN, —SCN, —NCS, —SF$_5$, —CF$_3$, —OCF$_3$, —OCHF$_2$ or —OCH$_2$F;

L is hydrogen or halogen;

X is hydrogen, or is alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$ or at least monosubstituted by halogen, and wherein one or more CH$_2$ groups are, optionally, each, independently of one another, replaced by —O—, —S—, —CO—, —COO—, —OCO— or —OCO—O— in such a way that heteroatoms are not directly adjacent, or is halogen, —CN, —SCN or —NCS;

Y, U and W, independently of one another, are each hydrogen, or are alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$ or at least monosubstituted by halogen, and wherein one or more CH$_2$ groups are, optionally, each, independently of one another, replaced by —O—, —S—, —CO—, —COO—, —OCO— or —OCO—O— in such a way that heteroatoms are not directly adjacent;

Z is in each case, independently of one another, a single bond, —CF$_2$O—, —OCF$_2$—, —CH$_2$CH$_2$—, —CF$_2$CF$_2$—, —C(O)O—, —OC(O)—, —CH$_2$O—, —OCH$_2$—, —CF=CH—, —CH=CF—, —CF=CF—, —CH=CH— or —C≡C—;

n is 0, 1, 2 or 3, p and q, independently of one another, are 0, 1, 2 or 3, wherein n+p+q is 1–9.

2. A compound according to claim 1, wherein
A is in each case, independently of one another,

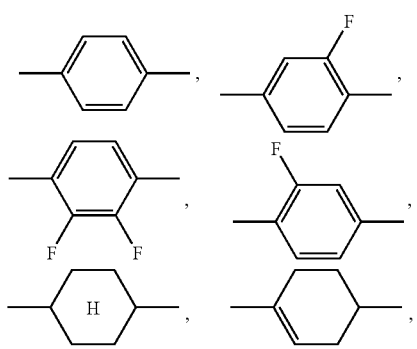

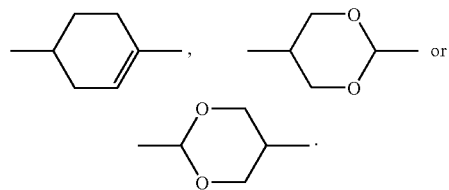

3. A compound according to claim 1, wherein R is in each case, independently of one another, alkyl having 1 to 7 carbon atoms radical, alkoxy having 1 to 7 carbon atoms or alkenyl radical having 2 to 7 carbon atoms.

4. A compound according to claim 2, wherein R is in each case, independently of one another, alkyl having 1 to 7 carbon atoms radical, alkoxy having 1 to 7 carbon atoms or alkenyl radical having 2 to 7 carbon atoms.

5. A compound according to claim 1, wherein Z is in each case, independently of one another, a single bond, —CF$_2$O—, —OCF$_2$—, —CF$_2$CF$_2$—, —CH=CH—, —CF=CH—, —CH=CF or —CF=CF—.

6. A compound according to claim 2, wherein Z is in each case, independently of one another, a single bond, —CF$_2$O—, —OCF$_2$—, —CF$_2$CF$_2$—, —CH=CH—, —CF=CH—, —CH=CF or —CF=CF—.

7. A compound according to claim 3, wherein Z is in each case, independently of one another, a single bond, —CF$_2$O—, —OCF$_2$—, —CF$_2$CF$_2$—, —CH=CH—, —CF=CH—, —CH=CF or —CF=CF—.

8. A compound according to claim 4, wherein Z is in each case, independently of one another, a single bond, —CF$_2$O—, —OCF$_2$—, —CF$_2$CF$_2$—, —CH=CH—, —CF=CH—, —CH=CF or —CF=CF—.

9. An indene compound according to claim 1, wherein
X is hydrogen, alkyl having 1 to 7 carbon atoms, alkoxy having 1 to 7 carbon atoms, alkenyl having 2 to 7 carbon atoms, or halogen,
Y is hydrogen, alkyl having 1 to 7 carbon atoms, alkoxy having 1 to 7 carbon atoms, or alkenyl having 2 to 7 carbon atoms,
U and W are each hydrogen,
and
n+p+q is 1 or 2.

10. An indene compound according to claim 2, wherein
X is hydrogen, alkyl having 1 to 7 carbon atoms, alkoxy having 1 to 7 carbon atoms, alkenyl having 2 to 7 carbon atoms, or halogen,
Y is hydrogen, alkyl having 1 to 7 carbon atoms, alkoxy having 1 to 7 carbon atoms, or alkenyl having 2 to 7 carbon atoms,
U and W are each hydrogen,
and
n+p+q is 1 or 2.

11. An indene compound according to claim 3, wherein
X is hydrogen, alkyl having 1 to 7 carbon atoms, alkoxy having 1 to 7 carbon atoms, alkenyl having 2 to 7 carbon atoms, or halogen,
Y is hydrogen, alkyl having 1 to 7 carbon atoms, alkoxy having 1 to 7 carbon atoms, or alkenyl having 2 to 7 carbon atoms,
U and W are each hydrogen,
and
n+p+q is 1 or 2.

12. An indene compound according to claim 5, wherein

X is hydrogen, alkyl having 1 to 7 carbon atoms, alkoxy having 1 to 7 carbon atoms, alkenyl having 2 to 7 carbon atoms, or halogen, Y is hydrogen, alkyl having 1 to 7 carbon atoms, alkoxy having 1 to 7 carbon atoms, or alkenyl having 2 to 7 carbon atoms, U and W are each hydrogen, and n+p+q is 1 or 2.

13. A compound according to claim 1, wherein U and W are each hydrogen.

14. A liquid-crystalline medium comprising at least two liquid-crystalline compounds, wherein at least one of said liquid-crystalline compounds is a compound according to claim 1.

15. In an electro-optical display element containing a liquid-crystalline medium, the improvement wherein said medium is one according to claim 14.

16. In a method of generating an electro-optical effect using an electro-optical display element, the improvement wherein said electro-optical display element is one according to claim 15.

17. An indene compound according to claim 3, wherein p and q are each O, W, U and Y are each H, L is H or F, and X is H or F.

18. An indene compound according to claim 17, wherein L is F, n is 1, 2 or 3, and T is 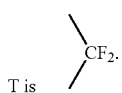

19. An indene compound according to claim 1, wherein X is hydrogen, alkyl having 1 to 7 carbon atoms, alkoxy having 1 to 7 carbon atoms, alkenyl having 2 to 7 carbon atoms, F, —CN, —SCN, or —NCS.

20. An indene compound according to claim 1, wherein T, L and X contain 2 to 4 F atoms.

21. An indene compound according to claim 1, wherein n+p+q is 1 or 2.

22. An indene compound according to claim 1, wherein n is 1.

23. A liquid crystalline compound, having a negative dielectric anisotropy, selected from formulae Ia–Ip:

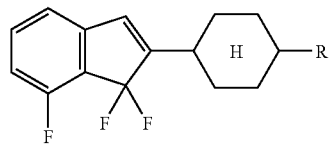
(Ia)

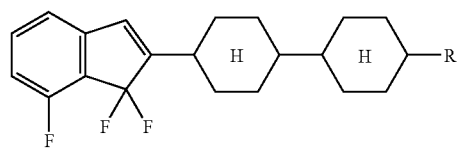
(Ib)

-continued

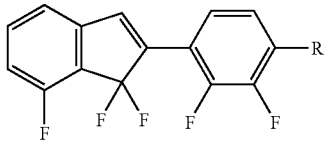
(Ic)

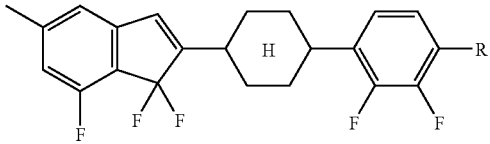
(Id)

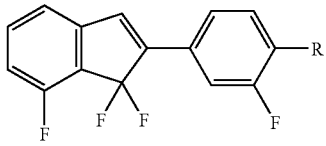
(Ie)

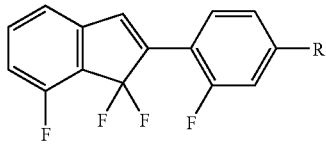
(If)

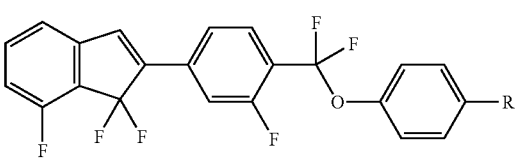
(Ig)

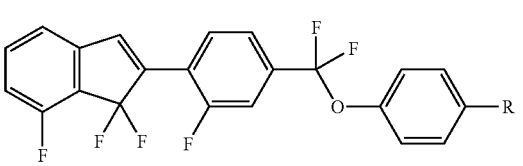
(Ih)

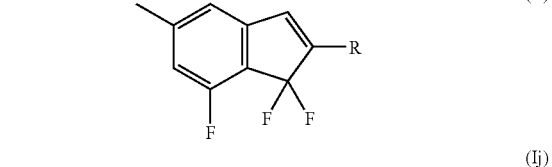
(Ii)

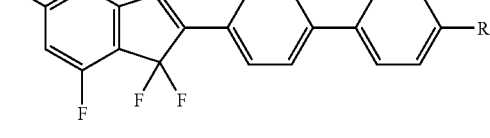
(Ij)

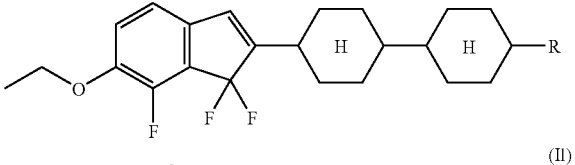
(Ik)

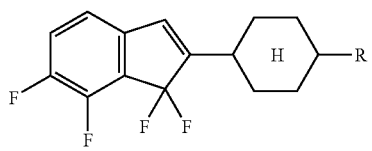
(Il)

-continued

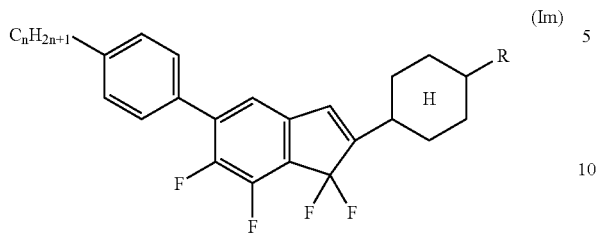
(Im)

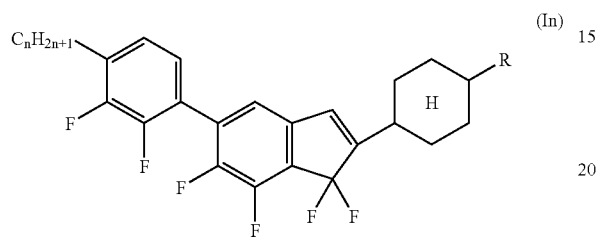
(In)

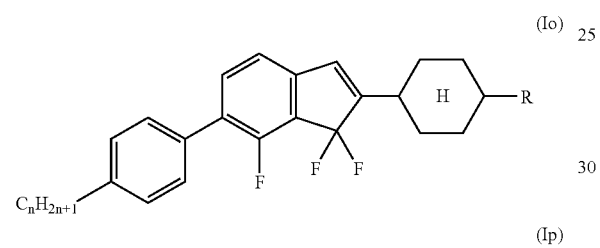
(Io)

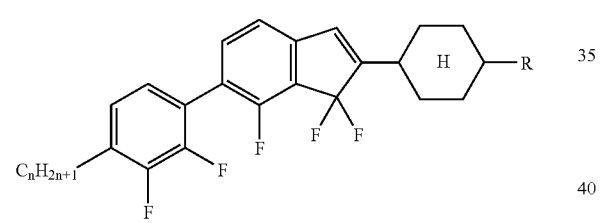
(Ip)

wherein
R is in each case, independently of one another, an alkyl having 1 to 7 carbon atoms, alkenyl having 2 to 7 carbon atoms, or alkoxy having 1 to 7 carbon atoms, and
n is 1, 2, 3, 4, 5, 6 or 7.

24. A liquid-crystalline medium comprising at least two liquid-crystalline compounds, wherein at least one of said liquid-crystalline compounds is a compound according to claim 22.

25. In an electro-optical display element containing a liquid-crystalline medium, the improvement wherein said medium is one according to claim 24.

26. In a method of generating an electro-optical effect using an electro-optical display element, the improvement wherein said electro-optical display element is one according to claim 25.

27. An indene compound according to claim 1, wherein said compound is a liquid crystalline compound.

28. An indene compound according to claim 2, wherein n+p+q is 1 or 2.

29. An indene compound of formula (I) having a negative dielectric anisotropy:

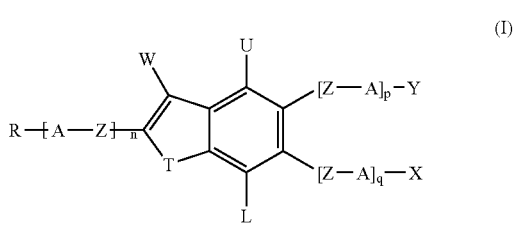
(I)

wherein:
T is in each case, independently of one another,

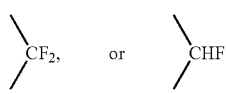

A is in each case, independently of one another, 1,4-phenylene, in which one or two =CH— groups are each, optionally, replaced by =N—, and which is unsubstituted or monosubstituted to tetrasubstituted, independently of one another, by halogen, —CN, —CH$_3$, —CH$_2$F, —CHF$_2$, —CF$_3$, —OCH$_3$, —OCH$_2$F, —OCHF$_2$ or —OCF$_3$, or is 1,4-cyclohexylene, 1,4-cyclohexenylene or 1,4-cyclohexadienylene, in which one or two —CH$_2$— groups are each, optionally, independently of one another, replaced by —O— or —S—, and which is unsubstituted or mono- or polysubstituted by halogen;

R is in each case, independently of one another, hydrogen, or is alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$, or at least monosubstituted by halogen, an wherein one or more CH$_2$ groups are, optionally, each, independently of one another, replaced by —O—, —S—, —CO—, —COO—, —OCO— or —OCO—O— in such a way that heteitiatoms are not directly adjacent, or is halogen, —CN, —SCN, —NCS, —SF$_5$, —CF$_3$, —OCF$_3$, —OCHF$_2$ or —OCH$_2$F;

L is hydrogen or halogen;

X is hydrogen, or is alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$ or at least monosubstituted by halogen, and wherein one or more CH$_2$ groups are, optionally, each, independently of one another, replaced by —O—, —S—, —CO—, —COO—, —OCO— or —OCO—O— in such a way that heteroatoms are not directly adjacent, or is halogen, —CN, —SCN or —NCS;

Y, U and W, independently of one another, are each hydrogen, or are alkyl having 1 to 15 carbon atoms, alkoxy having 1 to 15 carbon atoms, alkenyl having 2 to 15 carbon atoms or alkynyl having 2 to 15 carbon atoms, which in each case is unsubstituted, monosubstituted by —CF$_3$ or at least monosubstituted by halogen, and wherein one or more CH$_2$ groups are, optionally, each, independently of one another, replaced by —O—, —S—, —CO—, —COO—, —OCO— or —OCO—O— in such a way that heteroatoms are not directly adjacent;

Z is in each case, independently of one another, a single bond, —CF$_2$O—, —OCF$_2$—, —CH$_2$CH$_2$—, —CF$_2$CF$_2$—, —C(O)O—, —OC(O)—, —CH$_2$O—, —OCH$_2$—, —CF=CH—, —CH=CF—, —CF=CF—, —CH=CH— or —C≡C—;

n is 1, 2 or 3, and p and q, independently of one another, are 0, 1, 2 or 3.

30. A compound according to claim 10, wherein R is in each case, independently of one another, alkyl having 1 to 7 carbon atoms radical, alkoxy having 1 to 7 carbon atoms or alkenyl radical having 2 to 7 carbon atoms, and Z is in each case, independently of one another, a single bond, —CF$_2$O—, —OCF$_2$—, —CF$_2$CF$_2$—, —CH=CH—, —CF=CH—, —CH=CF or —CF=CF—.

* * * * *

UNITED STATES PATENT AND TRADEMARK OFFICE
CERTIFICATE OF CORRECTION

PATENT NO. : 7,182,885 B2
APPLICATION NO. : 10/406569
DATED : February 27, 2007
INVENTOR(S) : Lars Lietzau et al.

It is certified that error appears in the above-identified patent and that said Letters Patent is hereby corrected as shown below:

Column 19, line 11, reads "halogen, an" should read --halogen, and--
Column 20, line 14, delete "radical"
Column 21, line 27, reads "are each O," should read -- are each 0,--
Column 24, line 40, reads "halogen, an" should read -- halogen, and --
Column 26, line 3, delete "radical"

Signed and Sealed this

Twentieth Day of November, 2007

JON W. DUDAS
*Director of the United States Patent and Trademark Office*